United States Patent
Lehr

(10) Patent No.: US 9,062,333 B2
(45) Date of Patent: Jun. 23, 2015

(54) METHOD AND APPARATUS FOR TRANSFORMING WASTE INTO FUEL ETHANOL

(75) Inventor: Larry L. Lehr, Waco, TX (US)

(73) Assignee: ENVIRONMENTAL QUALITY MANAGEMENT ASSOCIATES, Waco, TX (US)

( * ) Notice: Subject to any disclaimer, the term of this patent is extended or adjusted under 35 U.S.C. 154(b) by 284 days.

(21) Appl. No.: 12/856,920

(22) Filed: Aug. 16, 2010

(65) Prior Publication Data

US 2011/0039318 A1 Feb. 17, 2011

Related U.S. Application Data

(60) Provisional application No. 61/233,924, filed on Aug. 14, 2009.

(51) Int. Cl.
| | |
|---|---|
| C12P 7/06 | (2006.01) |
| C12P 7/08 | (2006.01) |
| C12P 7/10 | (2006.01) |
| C12P 19/14 | (2006.01) |
| C12M 1/00 | (2006.01) |
| C12P 19/02 | (2006.01) |

(52) U.S. Cl.
CPC ............... *C12P 19/14* (2013.01); *C12M 43/02* (2013.01); *C12M 45/04* (2013.01); *C12M 45/20* (2013.01); *C12P 7/10* (2013.01); *C12P 19/02* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 4,273,621 | A | * | 6/1981 | Fornoff .......................... 203/19 |
| 4,769,112 | A | * | 9/1988 | Wheldon ........................ 203/19 |
| 2006/0177916 | A1 | * | 8/2006 | Stewart et al. ................ 435/161 |
| 2007/0218541 | A1 | * | 9/2007 | Denney et al. ................ 435/267 |
| 2008/0020089 | A1 | * | 1/2008 | Pearson .......................... 426/14 |
| 2009/0004714 | A1 | * | 1/2009 | Norholm et al. .............. 435/165 |

OTHER PUBLICATIONS

Liimatainen et al., Proceedings of the Waste Minimization and Resources Use Optimization Conference, Jun. 10, 2004, University of Oulu, Finland. Oulu University Press: Oulu. p. 123-129.*
Oleskowicz-Popiel et al. Bioresource Technology 99 (2008) 5327-5334.*
Sanchez et al. Bioresource Technology 99 (2008) 5270-5295.*

* cited by examiner

*Primary Examiner* — Chris R Tate
*Assistant Examiner* — Douglas F White
(74) *Attorney, Agent, or Firm* — Chaney P. Singleton; Chalker Flores, LLP

(57) ABSTRACT

The present invention describes substrates (feedstocks) used in the production of fuel ethanol and describes the process by which the alcohol is produced. The inventors process animal, vegetable, industrial food waste or a mixture of wastes in a process involving saccharification and fermentation reactions to produce a mixture of fuel ethanol water and carbon-dioxide, which is subsequently separated to recover 95 vol. % ethanol.

8 Claims, 1 Drawing Sheet

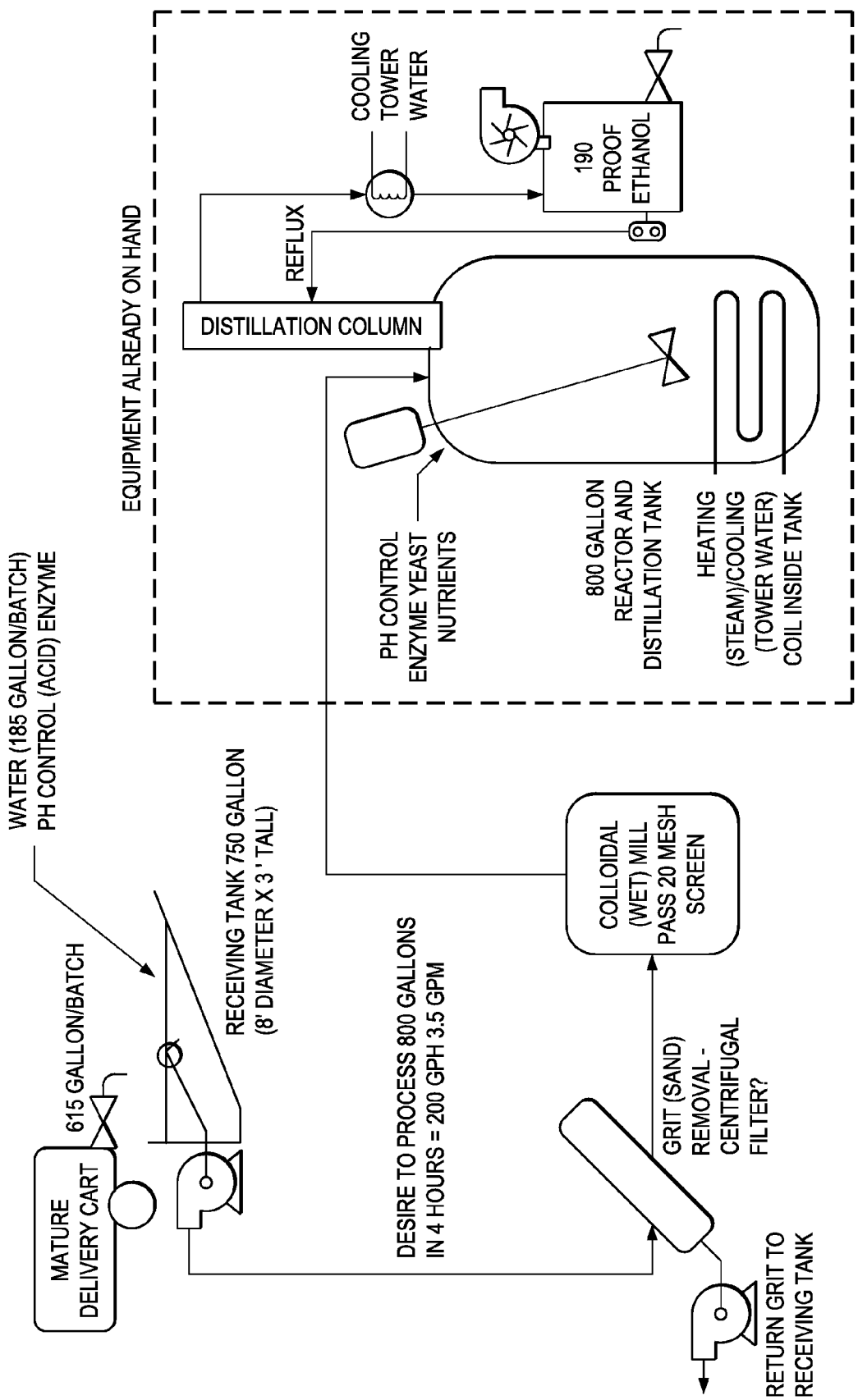

METHOD AND APPARATUS FOR TRANSFORMING WASTE INTO FUEL ETHANOL

CROSS-REFERENCE TO RELATED APPLICATIONS

This application claims priority to U.S. Provisional Application Ser. No. 61/233,924, filed Aug. 14, 2009, the entire contents of which are incorporated herein by reference.

TECHNICAL FIELD OF THE INVENTION

The present invention relates in general to the field of waste treatment, and more particularly, to the process and equipment for transforming wastes (e.g., feedstock) into fuel ethanol.

STATEMENT OF FEDERALLY FUNDED RESEARCH

None.

BACKGROUND OF THE INVENTION

Without limiting the scope of the invention, its background is described in connection with ethanol production from animal and vegetable waste.

For example, U.S. Pat. No. 4,952,504 issued to Pavilon (1990) describes the production of ethanol and, more particularly, to conversion of biomass for producing ethanol. patent '504 is particularly applicable to conversion of wood and agricultural wastes to produce ethanol. The biomass slurry is hydrolyzed in a fuel fired hydrolysis heater, and the solids are separated from the hydrolyzed effluent. The effluent is fermented and subsequently distilled at substantially atmospheric pressure to produce ethyl alcohol vapor. The vapor is fed to a vacuum distillation tower for producing anhydrous ethyl alcohol.

United States Patent Application No. 20080213849 Stewart et al., (2008) discloses a method for producing ethanol from solid citrus waste by reducing the concentration of limonene in citrus waste to allow fermentation. The solid citrus waste is partially hydrolyzed and pasteurized by heating using a jet cooker and then injected into a flash tank to remove limonene. The heated citrus waste is then cooled, hydrolyzed with enzymes and fermented to ethanol. The remaining solids and liquids may be processed further to yield other byproducts. More particularly, the solids may be dried and pressed for use in cattle feed and the liquids may be further fermented or processed to yield additional ethanol, acetate, galacturonic acid monomers and polymers, five carbon sugars and other products.

SUMMARY OF THE INVENTION

The present invention describes a process involving saccharification and fermentation reactions to convert candy waste, bakery waste, vegetable waste, cow waste, poultry waste, hog waste, human waste, and paunch manure into fuel ethanol.

The present invention includes a method for processing one or more wastes prior to a waste treatment by mixing the waste with an excess of water in a mixing tank to form a suspension or a slurry, wherein the suspension or the slurry comprises a solution of one or more water-soluble waste components and one or more heavy and light components of the waste; allowing the suspension or the slurry to stand in the mixing tank for a specified period of time, wherein the one or more heavy components settle at the bottom of the mixing tank and the one or more light components float on the top; separating the heavy components from the bottom of the mixing tank through one or more openings at the bottom of the mixing tank, wherein the one or more openings are controlled manually or automatically; separating the light components from the top of the mixing tank by one or more physical methods, wherein the physical methods comprise using a filter, a mesh, a screen, a decantation, an aspiration or any combinations thereof; pumping the solution of water-soluble waste to a heated reactor; adding a measured quantity of water to the solution of water-soluble waste to a heated reactor; adding an α-amylase, an amyloglucosidase, or a mixture of both to the heated reactor, wherein the α-amylase, the amyloglucosidase, or the mixture liquefies the one or more carbohydrates in the water-soluble waste; maintaining a controlled temperature, a controlled pH, and a controlled pressure in the heated reactor; adding one or more beta enzymes to the heated reactor; wherein the one or more beta enzymes converts the liquefied one or more carbohydrates in the water-soluble waste to one or more fermentable sugars; and cooling the heated reactor.

The present invention includes a method for producing fuel ethanol from one or more animal wastes, one or more vegetable wastes, one or more industrial food wastes or a mixture by providing a heated reactor, wherein the heated reactor contains the animal wastes, the vegetable wastes, the industrial food wastes or the mixture; adding a measured quantity of water to the animal wastes, the vegetable wastes, the industrial food wastes, or the mixture contained in the heated reactor; and adding of one or more yeast species to the cooled reactor, wherein the one or more yeast species anaerobically ferment the one or more fermentable sugars to fuel ethanol and carbon dioxide, wherein the fuel ethanol is mixed with water.

The present invention includes a method of producing fuel ethanol from one or more wastes or a mixture of wastes by milling or grinding the one or more wastes or the mixture of wastes; mixing the milled or ground wastes with a controlled quantity of water to form a mash; pumping the mash to a precook vessel maintained at a specified temperature; heating the mash to a specified temperature in the precook vessel by the injection of a saturated steam at a specified pressure; pumping the heated mash to a cooking vessel; holding the heated mash for a specified time for the breakdown of the one or more carbohydrates in the heated mash; cooling the heated mash to a specified temperature by vacuum flashing; adding an amylase, an amylogluosidases or both to the cooled mash for converting the broken down carbohydrates to one or more fermentable sugars; lowering the pH by dilution using an effluent or a thin stillage; cooling the diluted mash by using one or more heat exchangers; pumping the cooled mash to one or more fermentation reactors arranged in a network; adding one or more species of yeast to the fermentation reactors; and converting the one or more fermentable sugars to form one or more fermentation products; wherein the products comprises the fuel ethanol water mixture and carbon dioxide.

The present invention includes a system for processing animal wastes, vegetable wastes, industrial food wastes or a mixture of wastes including one or mixing tanks, wherein the mixing tank is used for blending a milled animal waste, vegetable waste, industrial food waste or a mixture of wastes with water to form a mash; a precook vessel, wherein the mash is heated with an injection of live steam; a cooking vessel, wherein the mash is held for the one or more carbohydrates to break up into one or more simpler sugars; one or more reactors for converting the simpler sugars into one or more fermentable sugars in the presence of one or amylases, amyloglucosidases, or a mixture; a fermentation reactor network; wherein the network comprises at least one set of two reactors with an attached heat exchanger and a circulating pump; a storage tank, wherein the mixture of fuel-ethanol water and carbon-dioxide are stored prior to a separation; a recovery or a separation system comprising two distillation columns and a stripping column; and one or more ancillary equipments, wherein the ancillary equipment is selected from a group consisting of blenders, steam injectors, steam ejectors, vacuum generators, condensers, pumps, heat exchangers, cooling towers, flash drums, and reboilers,

BRIEF DESCRIPTION OF THE DRAWINGS

For a more complete understanding of the features and advantages of the present invention, reference is now made to the detailed description of the invention along with the accompanying figures and in which:

FIG. 1 is a schematic of one embodiment of the processing plant of the instant invention.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention identifies the substrates (feedstocks) used in the production of fuel ethanol and describes the process by which the alcohol is produced. The inventors have successfully transformed candy waste, bakery waste, vegetable waste, cow waste, poultry waste, hog waste, human waste, and paunch manure into fuel ethanol.

A trend away from small-family owned farms into large-scale animal production operations has increased the concentration of animal waste generated from Confined Animal Feed Operations (CAFOs). The State of Texas produces an estimated 220 billion pounds of manure/year, which subsequently impacts air and water quality thereby creating a public health hazard. There are also a number of industrial waste streams generated from food manufacturers that are amenable to conversion to fuel ethanol.

Animal waste is typically composed of inorganic nutrients, i.e. nitrogen, phosphorus, etc. and carbohydrates. Recent data suggests that at least 338 miles of Texas streams and over 23,000 acres of lakes have been negatively impacted. Manures are carbon based compounds amenable as substrates (feedstock) for conversion to fermentable sugars and bio-transformation to ethyl alcohol that can be used as a fuel. There is an active and recognized national market for ethyl alcohol.

The strategy of transforming CAFO waste is advantageous to waste generators and the regional community. The use of animal waste as a feedstock not only reduces the external costs paid by the local community related to pollution remediation but reduces the contingent liability faced by CAFO managers while simultaneously providing a value-added revenue stream to their livestock operation.

There are 151 ethanol plants in the US, most use small grains, i.e. corn or milo, to produce fuel ethanol. Plants are typically sized at a minimum of 20 million gallons/year. Corn prices are near historic highs thus forcing the cost of ethanol upwards and reducing the profit margin resulting from the difference in production cost, capital cost, and market price. Most CAFO producers and industrial waste generators cannot economically justify converting their waste into ethanol because of economies of scales.

The facility described in the present invention represents a 'boutique' distillery designed to manage waste from relatively small generators to produce ethanol on the order of 1-5 million gallons/years.

Transformation of selected industrial waste streams has been accomplished on a macro scale by the inventors. Transformation of food wastes, turkey, chicken, and dairy waste has been accomplished on a bench scale using the process of the present invention. Ethanol yields range from 25-80 gallons per ton. The sample data is shown in Table 1 below.

TABLE 1

| Feedstock | Samples Converted | Extrapolated Yield (gal) |
|---|---|---|
| Grocery Wastes | 15 | 55 |
| Raw beet pulp | 3 | 35 |
| Candy Waste | 25 | 57 |
| Dairy Waste | 3 | 48 |
| Corn Chip | 1 | 50 |
| Turkey waste | 5 | 62 |

Change in physical state: Conversion of the wastes (e.g., feedstock) was achieved by the addition of water to the feedstock in a heated reactor. The amount of water is a function of the physical properties of the feedstock. The carbohydrates and cellulose in the feedstock are liquefied by the addition of alpha amylase enzymes in a specified environment of temperature, pH, and pressure. Once liquefaction has occurred, a beta enzyme (transforms carbohydrates to fermentable sugars) is added, temperature, pH, and pressure are modified, and the liquefied carbohydrates are transformed to fermentable sugars, primarily glucose. The solution is cooled to approximately 85° F. and the yeasts are allowed to ferment anaerobically.

Anaerobic fermentation forces the yeasts into a different metabolic pathway thereby stimulating the production of ethyl alcohol and carbon dioxide. There is a 1:1 stoichiometric ratio (by weight) between ethyl alcohol and carbon dioxide production. The solution will achieve an approximate concentration of 10% ethyl alcohol, which kills the yeast.

The 10% ethanol-90% water solution is then pumped to a distillation column to produce approximately 190 proof (95%) ethanol. The remaining 5% water is removed by a molecular sieve which 'breaks' the azeotrope thereby producing 200 proof (100% or anhydrous) ethyl alcohol. The energy for distillation will be generated from a methane digester that uses manure as the feedstock.

Ruminant and poultry rations are typically blended from of a variety of plant carbohydrates (Hall, 2001). Ruminants and poultry do not efficiently digest the nutrients in the rations. These nutrients, primarily carbohydrates and cellulose, can be readily converted to fermentable sugars by enzymatic or acid hydrolysis and used as a substrate for the production of ethyl alcohol by yeast.

Advantages of waste as a feedstock: The greatest cost in the production of ethyl alcohol is feedstock. Historically, small grains or other agricultural commodities, i.e. potatoes or beets, have been used as feedstock. Cost is a function of ethanol yield vs. the cost per unit of commodity. Grain prices recently (March 2007) were at a 40-year high due to a perceived shortage of corn to meet the growing demand for alcohol plants and cattle feed operations. The resultant prices, reaching $4.50/bushel, equate to a feedstock production cost of $1.73/gallon. Wastes are typically inexpensive, and in many cases have represented a liability to the producer. Cost of ethanol from waste ranges from $0.45-$0.90/gallon.

Production of ethyl alcohol: Ethyl alcohol is produced by anaerobic metabolism of yeast that will convert simple sugars into ethanol and carbon dioxide in a 1:1 stoichiometric ratio. Ethanol produced by fermentation ranges in concentration from a few percent up to about 14 percent. It is normally concentrated by distillation of aqueous solutions, but the composition of the vapor is 96 percent ethanol and 4 percent water. Dehydrating agents can be used to remove the remaining water and produce absolute (200-proof) product.

Process overview: Ethyl alcohol can be produced from a variety of sources, including fermentation of carbohydrates derived from starch crops such as grain and potatoes, from sugar crops such as cane and beets, from cellulosic agricultural residues such as bagasse and corn stalks, and wood and wood by-products. It can also be produced by hydration of ethylene or from synthesis gas containing hydrogen and carbon monoxide. In a number of countries, such as Brazil, considerable progress has been made in using ethanol to supplement gasoline. In addition, the abundance of grains produced in the United States and other countries has enhanced the attractiveness of converting a portion of these grains to ethyl alcohol for blending with gasoline as an octane enhancement agent or for use as a feedstock in the synthesis of other chemicals.

The feedstock is converted to ethyl alcohol by two biological processes: saccharification and fermentation. In saccharification, the polymeric structure of starch (a polysaccharide) is hydrolyzed in the presence of the enzymes (biological catalysts) α-amylase and amyloglucosidase. The primary products of hydrolysis are maltose (a disaccharide consisting of two glucose units) and oligomers consisting of several glucose units.

$$(C_6H_{10}O_5) ---- (enzyme) \rightarrow C_{12}H_{22}O_{11} + (C_6H_{10}O_5)$$

Starch Maltose Oligomers (1)

The fermentation process is based on the growth of a yeast culture that converts maltose to ethyl alcohol and carbon dioxide:

$$C_{12}H_{22}O_{11} + H_2O (+yeast) \rightarrow 4C_2H_5OH + 4CO_2 + (H_2O + yeast)$$ (2)

As the yeast culture grows, 0.0794 lb. of yeast is produced for every lb. ethyl alcohol formed, and 0.291-lb. water is produced for every lb. of yeast formed. The residue from the alcohol recovery and dehydration operation can be further processed to recover distillers' dried grains and solubles (DDGS). The yeast solids become a part of the by-product grains, and the sale of DDGS as animal feed improves process economics and minimizes waste disposal problems.

Conversion, fermentation and distillation: Production techniques for fermentation ethanol from small grains are well established. Transformation of manure to fermentable sugars, is feasible as indicated in recent laboratory studies, the subsequent fermentation, distillation, and azeotropic separation are standard. The detailed process description is provided below and clarifies the role of the manure, paunch manure, candy waste, and selected industrial feedstocks in the process.

Manure and/or industrial food waste will be milled and the resulting meal conveyed to a mixing tank where it is blended with recycled condensates and water to produce a mash. The total water input to this tank is controlled to produce 22 gal of mash per hundred weight of manure input. The specific gravity of the mash is approximately 1.1. From the mixing tank, the slurry flows to a precook vessel, which is maintained at 145° F. The condensates, which have been added hot to the mixing tank, yield a mash at 100° F. Live saturated steam at 15 psig is added to the precook vessel to increase the mash temperature to 145° F. Live steam is steam injected directly into a process vessel. The temperatures used here are for illustrative purposes and the skilled artisan will understand that other temperatures and temperature ranges.

Mash from the precooking vessel is heated to 230° F. by condensing saturated steam at 15 psig, and then to 320° F. with saturated 150-psig live steam. The mash is then sent to a cooking tank and held there long enough for the starch structure to be broken down in preparation for the saccharification reactions. The cooked mash is flashed to 15 psig to produce saturated steam and a concentrated mash, which is cooled to 145° F. by flashing to a vacuum. The flash-tank vacuum is maintained by drawing the vapor into a condenser where most of the steam is condensed and passing the remaining uncondensed vapor to a steam ejector. Steam at 150 psig is fed to the ejector along with the uncondensed vapor, and the resulting mixture is sent to a condenser operating at 15 psig. The ratio of vapor drawn from the flash condenser to 150-psig steam fed to the ejector is 0.04 lb. vapor/lb. steam. Approximately 30 lb./h of vapor is drawn into the ejector from the flash condenser. All condensates from these units are pumped back to the mash mixing tank.

Mash from the vacuum flash is mixed with a small amount of fungal amylase, and the mixture is sent to the saccharification reactors where the starch is converted at 140° F. to fermentable sugars. Thin stillage recycled from a downstream unit is added to the liquor from the saccharification reactors to lower the pH, provide yeast nutrients, and obtain a final mash volume of 25 gal per bushel of corn fed to the process. The volume of the thin stillage added is 16% of the final mash volume going to the fermenters. The mixture of converted mash and thin stillage is cooled in heat exchangers to 100° F. by cooling-tower water at 85° F., and then to 85° F. by well water at 60° F. The temperature increases of both cooling water streams are limited to 25° F.

The cooled mash is fed to the fermentation reactors, which are operated in a batch mode. The reactor network comprises of eight vessels. The vessels are arranged in sets of two with one heat exchanger and circulation pump for each set of fermenters. Liquid loading is 90% of vessel capacity. Cooling is needed for only about 24-h out of the 48-h fermentation cycle, which makes it possible for one exchanger to service two fermenters. The fermenters are filled on an 8-h cycle; in other words, the flow rate of mash is sufficient to fill a single reactor every eight hours.

Yeast is added to each fermentation batch. During fermentation, heat is released by the exothermic conversion of sugars to ethanol and carbon dioxide, and the batch temperature is allowed to increase from 85° F. to 95° F. Removal of heat from the mash as it is recirculated through the heat exchangers is used to prevent the temperature from increasing above 95° F. Well water at 60° F. is the cooling fluid used in these exchangers, and each fermenter requires a flow of about 2400 gal/min during the peak period. The temperature increase of the well water is limited to 25° F.

The fermentation products are sent to a storage vessel from which dilute alcohol is pumped at 90° F. and 1 atm and heated to 280° F. by condensing 150-psig saturated steam. The dilute alcohol is then flashed to separate essentially all of the carbon dioxide. Water and alcohol vaporized with the carbon dioxide are condensed and returned to the flash drum. The liquid leaving the flash drum is at 250° F. and consists of 9.1 wt % alcohol, 6.9 wt % soluble and suspended solids, and water. This liquid is fed to a recovery system consisting of two distillation columns and one stripping column.

Feed enters each distillation column at a location between the top and bottom, and two product streams are withdrawn. A vapor stream is removed from the top of the column and condensed. A portion of the condensate (reflux) is returned to the top of the column, and the remainder is taken as overhead product or distillate. A liquid stream leaves the bottom of the column and goes to a reboiler that vaporizes a portion of the liquid. The generated vapor is returned to the column as boilup, and the remaining liquid is taken as product and is referred to as bottoms. In the stripping column (stripper), the liquid feed is introduced at the top of the column, and two product streams are withdrawn. One of the product streams is a vapor leaving the top of the column and the other is a liquid that leaves the bottom of the column and is fed to a reboiler. The reboiler generates a vapor stream, which is returned to the stripper as boilup, and a liquid bottoms product.

The dilute liquid from the flash tank is fed to the first distillation column, which is operated at 50 psig and is known as the ethanol concentrator. Heat is supplied to the ethanol concentrator by condensing approximately 110,000 lb/hour of 150-psig saturated steam in the reboiler. Condensate from the reboiler is saturated at 150 psig. The distillate and reflux are saturated liquids at 250° F. and contain 95 volume percent (190-proof) ethyl alcohol. The bottoms from the column are at a temperature of about 305° F., and contain all of the solids fed to the column and approximately 0.02 weight percent alcohol on a solids-free basis.

An azeotrope containing two or more components is a mixture whose bubble point is greater or less than all pure-component bubble points. If an azeotrope is encountered in distillation, its composition represents a limit to the separation or concentration that can be achieved. In the system at hand, the distillate from the ethanol concentrator has a composition approaching that of the azeotrope formed between ethanol and water, 89 mole percent ethanol and 11 percent water. Further purification of the ethyl alcohol in this stream can be accomplished only by breaking the azeotrope, which is done in this case by the use of a molecular sieve. The sieve is a 3 angstrom engineered silica compound that adsorbs the water molecule thereby breaking the hydrogen bonds holding the alcohol group.

Operating procedures: Different types of wastes, food wastes, cow, turkey, chicken, hog, or human manure require alternative processing strategies as a function of age, carbohydrate value, pH, moisture content, or mass. An example of the operation procedures for one waste stream, broiler chicken manure, is provided as FIG. 2.

In another embodiment turkey Manure was used. In this embodiment 800 Gallons of water was placed into the Demo tank and ½ gallon of Muriatic acid was added. The tank was heated to 140 F and agitated. At least 672 pounds of turkey manure was slowly added paying close attention of the viscosity/thickness. The pH was adjusted to between 4.2-4.5 using muriatic acid. A sample was taken and combined with 1 quart of Cellulase enzyme and 1 quart of Alpha enzyme and heated to a temperature of 140 degrees F. for 1 hour. Another sample was taken and heated to a temperature of 185 degrees F. for 1 hour and then cooled to a temperature of 140 degrees F. A sample was taken and combined with 1 pint Glucoamylase and 1 pint Cellulase enzyme. A yeast Prop. Was made at a cool temperature of 88 degrees F. and 0.5 grams of antibiotic, 13 pounds of Nutrients, and 1.5 pounds of yeast was added. Compressed air was also added and the temperature maintain at 88 degrees Fahrenheit with the compressed air on for 8 hours. After the 8 hours the yeast viability, pH, temp, and Brix was checked. 50 pounds of nutrients, and enough ammonia was added to bring the pH up to 4.5. Over the course of the next hour the temperature was raised to 94 degrees F. The compressed air was turned off and considered as time point 0 hour. Samples were taken at 10 hours, 18 hours, 25 hours, 39 hours, 45 hours, and 55 hours and check for yeast viability, pH, temp, and Brix. After 72 hours fermentation has slowed down significantly and is ready for distillation. Take the drop sample at this point.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for producing fuel ethanol from wastes comprising the steps of:
   providing a heated reactor;
   adding a waste mash of one or more animal wastes, one or more vegetable wastes, one or more industrial food wastes or a mixture thereof to the heated reactor;
   adding a measured quantity of water to the waste mash contained in the heated reactor;
   precooking the waste mash at about 145° F.;
   heating the waste mash to between about 230° F. and 320° F.;
   cooling the mash to between about 140° F. and 145° F. to form starch;
   adding one or more beta enzymes selected from a group consisting of α-amylases, amyloglucosidases, β-amylase, cellulases, and lignases to the waste mash;
   cooling the waste mash to about 85° F.;
   liquefying the waste;
   converting the one or more carbohydrates to one or more fermentable sugars comprising one or more disaccharides and one or more oligomer;
   adding of one or more yeast species to the cooled reactor;
   maintaining a temperature of between about 85-95 ° F.;
   forming fuel ethanol and carbon dioxide by anaerobic fermentation of the one or more fermentable sugars by the one or more yeast species;
   forming a mixture of the fuel ethanol and water;
   transferring the mixture to a distillation column;
   distilling the mixture to separate the fuel ethanol and the water to form a distilled fuel ethanol; and
   contacting the distilled fuel ethanol with one or more molecular sieves to remove residual water.

2. The method of claim 1, wherein the one or more animal wastes are selected from a group consisting of cow wastes, poultry wastes, hog wastes, turkey waste, chicken waste, dairy waste, human wastes, animal manure, algal biomass and fungal biomass.

3. The method of claim 1, wherein the measured quantity of water is determined by one or more physical properties of the animal wastes, the vegetable wastes, the industrial food wastes, or the mixture.

4. The method of claim 1, wherein the one or more molecular sieves are selected from a group consisting of activated carbon, desiccants, lime, silica gel, and zeolites.

5. The method of claim 1, wherein the disaccharide is maltose and the oligomer comprises of one or more glucose units.

6. The method of claim 1, wherein the one or more vegetable wastes are selected from a group consisting of fruit wastes, potatoes, sugar crops, cane, beets, bagasse, wood, and wood by-products.

7. The method of claim 1, wherein the one or more industrial food wastes are selected from a group consisting of candy waste, bakery waste, rice bran, bean curd refuse, soybean meals, bread, and steamed rice fodder.

8. A method for producing fuel ethanol from wastes comprising the steps of:
   providing a heated reactor;
   adding a waste mash of one or more animal wastes, one or more vegetable wastes, one or more industrial food wastes or a mixture thereof to the heated reactor;
   adding a measured quantity of water to the waste mash contained in the heated reactor;
   precooking the waste mash at about 145° F.;
   heating the waste mash to between about 230° F. and 320° F.;
   cooling the mash to between about 140° F. and 145° F. to form starch;
   adding one or more beta enzymes selected from a group consisting of α-amylases, amyloglucosidases, β-amylase, cellulases, and lignases to the waste mash;
   liquefying the waste;
   converting the one or more carbohydrates to one or more fermentable sugars comprising one or more disaccharides and one or more oligomer;
   cooling the waste mash to about 85° F.;
   adding of one or more yeast species to the cooled reactor;
   maintaining a temperature of between about 85-95 ° F.;
   forming fuel ethanol and carbon dioxide by anaerobic fermentation of the one or more fermentable sugars by the one or more yeast species;
   forming a mixture of the fuel ethanol and water;
   transferring the mixture to a distillation column;
   distilling the mixture to separate the fuel ethanol and the water to form a distilled fuel ethanol; and
   contacting the distilled fuel ethanol with one or more molecular sieves to remove residual water.

* * * * *